US008887912B2

(12) United States Patent
Chapin et al.

(10) Patent No.: US 8,887,912 B2
(45) Date of Patent: Nov. 18, 2014

(54) LIVING HINGE NEEDLE ASSEMBLY FOR MEDICAMENT DELIVERY DEVICE

(75) Inventors: David S. Chapin, Raleigh, NC (US); Daniel M. Stipe, Raleigh, NC (US); Sean P. Sullivan, Ridgewood, NJ (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 130 days.

(21) Appl. No.: 13/204,615

(22) Filed: Aug. 5, 2011

(65) Prior Publication Data

US 2012/0041380 A1 Feb. 16, 2012

Related U.S. Application Data

(60) Provisional application No. 61/344,537, filed on Aug. 16, 2010.

(51) Int. Cl.
| | | |
|---|---|---|
| *B65D 83/10* | (2006.01) | |
| *A61M 5/00* | (2006.01) | |
| *B65D 85/24* | (2006.01) | |
| *A61M 5/32* | (2006.01) | |
| *A61M 5/24* | (2006.01) | |

(52) U.S. Cl.
CPC ............ *A61M 5/3202* (2013.01); *A61M 5/002* (2013.01); *B65D 85/24* (2013.01); *A61M 5/3205* (2013.01); *A61M 5/008* (2013.01); *A61M 5/24* (2013.01)
USPC .......................................... 206/366; 206/365

(58) Field of Classification Search
CPC ......... B65D 1/30; A61M 5/002; Y10S 206/82
USPC .......... 206/363, 366, 365, 370; 215/236, 237, 215/238; 220/23.8, 837
See application file for complete search history.

(56) References Cited

U.S. PATENT DOCUMENTS

| | | | | | |
|---|---|---|---|---|---|
| 2,932,386 | A | * | 4/1960 | Meyer | 249/127 |
| 3,021,001 | A | * | 2/1962 | Donofrio | 220/23.4 |
| 3,074,540 | A | | 1/1963 | Beich et al. | |
| 3,114,455 | A | | 12/1963 | Claisse et al. | |
| 3,367,488 | A | * | 2/1968 | Hamilton | 206/365 |
| 3,757,983 | A | * | 9/1973 | McCarthy | 220/23.4 |
| 3,962,750 | A | * | 6/1976 | Buss et al. | 16/381 |
| 5,257,721 | A | * | 11/1993 | Smith et al. | 220/533 |
| 5,398,827 | A | * | 3/1995 | Armstrong et al. | 215/6 |
| 5,702,017 | A | * | 12/1997 | Goncalves | 220/23.4 |

(Continued)

FOREIGN PATENT DOCUMENTS

| | | |
|---|---|---|
| EP | 2 298 397 A1 | 3/2011 |
| GB | 649541 * | 1/1951 |

(Continued)

*Primary Examiner* — David Fidei
(74) *Attorney, Agent, or Firm* — Roylance, Abrams, Berdo and Goodman, LLP (57) ABSTRACT

A multi-pack assembly for containing and dispensing one or more new pen needles, and receiving and containing used pen needles after use, is provided, wherein a plurality of both new and used pen needles can be contained in a series of storage vessels, each secured to an adjacent storage vessel thereby forming an easily managed multi-pack assembly shape, and providing caps for each individual pen needle storage vessel to provide a sterility barrier and which can be opened independently of one another, and which can be closed in the same manner after use to prevent unwanted interaction with the used pen needles contained therein.

13 Claims, 7 Drawing Sheets

(56) References Cited

U.S. PATENT DOCUMENTS

| | | | | |
|---|---|---|---|---|
| 5,722,553 | A | * | 3/1998 | Hovatter ...................... 220/23.8 |
| 2006/0032769 | A1 | * | 2/2006 | Erickson et al. .............. 206/365 |
| 2010/0051636 | A1 | * | 3/2010 | Logel et al. ................... 220/834 |
| 2013/0105345 | A1 | * | 5/2013 | Van der Beek et al. ....... 206/366 |

FOREIGN PATENT DOCUMENTS

| | | |
|---|---|---|
| GB | 2 424 414 A | 9/2006 |
| JP | 6-321268 | 11/1994 |
| WO | WO 02/11797 A1 | 2/2002 |
| WO | WO 2007/132237 A1 | 11/2007 |

* cited by examiner

LIVING HINGE NEEDLE ASSEMBLY FOR MEDICAMENT DELIVERY DEVICE

CROSS-REFERENCE TO RELATED APPLICATIONS

This application claims the benefit under 35 U.S.C. §119 (e) of a U.S. provisional patent application of David Chapin et al. entitled "Living Hinge Needle Assembly For Medicament Delivery Device", Ser. No. 61/344,537, filed on Aug. 16, 2010, the entire content of said application being incorporated herein by reference.

FIELD OF THE INVENTION

The present invention relates to a storage assembly for pen needles of an injection apparatus. More particularly, the present invention relates to a storage assembly for storing both new and used pen needles of an injection apparatus.

BACKGROUND OF THE INVENTION

In certain circumstances, it is desirable to inject medication directly into human tissue. Typically, syringes or pen injection devices are used to inject medicaments into tissue areas, such as the intramuscular tissue layer, the subcutaneous tissue layer, and the intradermal tissue layer. The assembly and operation of such a pen injection device is described in U.S. Pat. No. 7,645,264, issued on Jan. 12, 2010, the entire contents of which are incorporated herein by reference.

Figure 1:
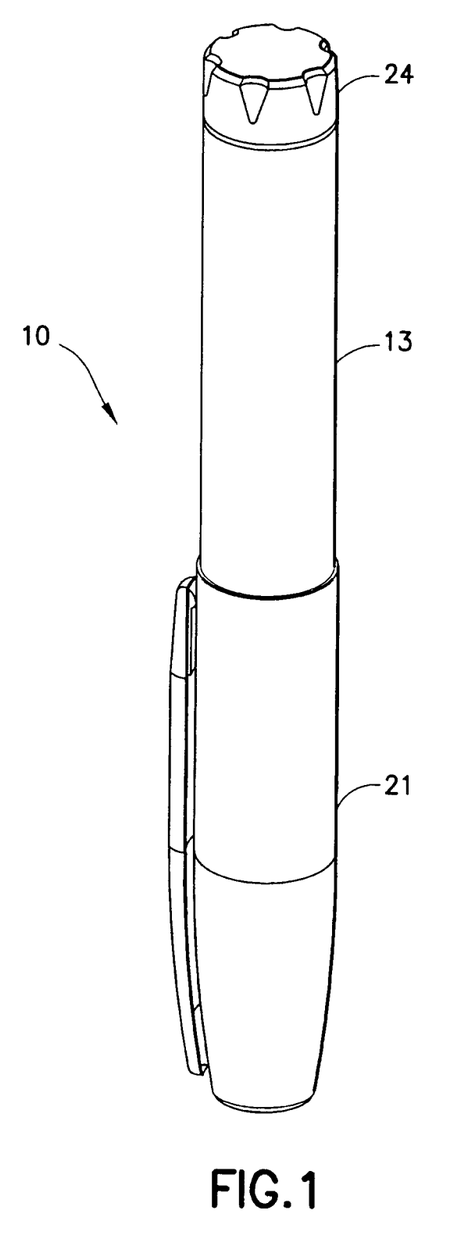
FIG. 1 is a perspective view of an assembled drug delivery pen for use with exemplary embodiments of the present invention.

Pen injection devices, such as the exemplary drug delivery pen 10 as shown in FIG. 1, provide the user a convenient way to carry a medicament supply. All of the required features and components for at least a single use are provided in the assembly, and in most cases, provide for multiple uses. To do so, the pen 10 typically comprises a dose knob/button 24, an outer sleeve 13, and a cap 21. The cap 21 covers a proximal end of the pen 10 and an injection needle attached thereto, and is used by the user to securely hold the drug delivery pen 10 in a shirt pocket, purse or other suitable location. The dose knob/button 24 allows a user to set the dosage of medication to be injected, and the outer sleeve 13 contains the driving mechanisms and supply, and further provides a gripping surface for the user to grip when injecting medication.

Figure 2A:
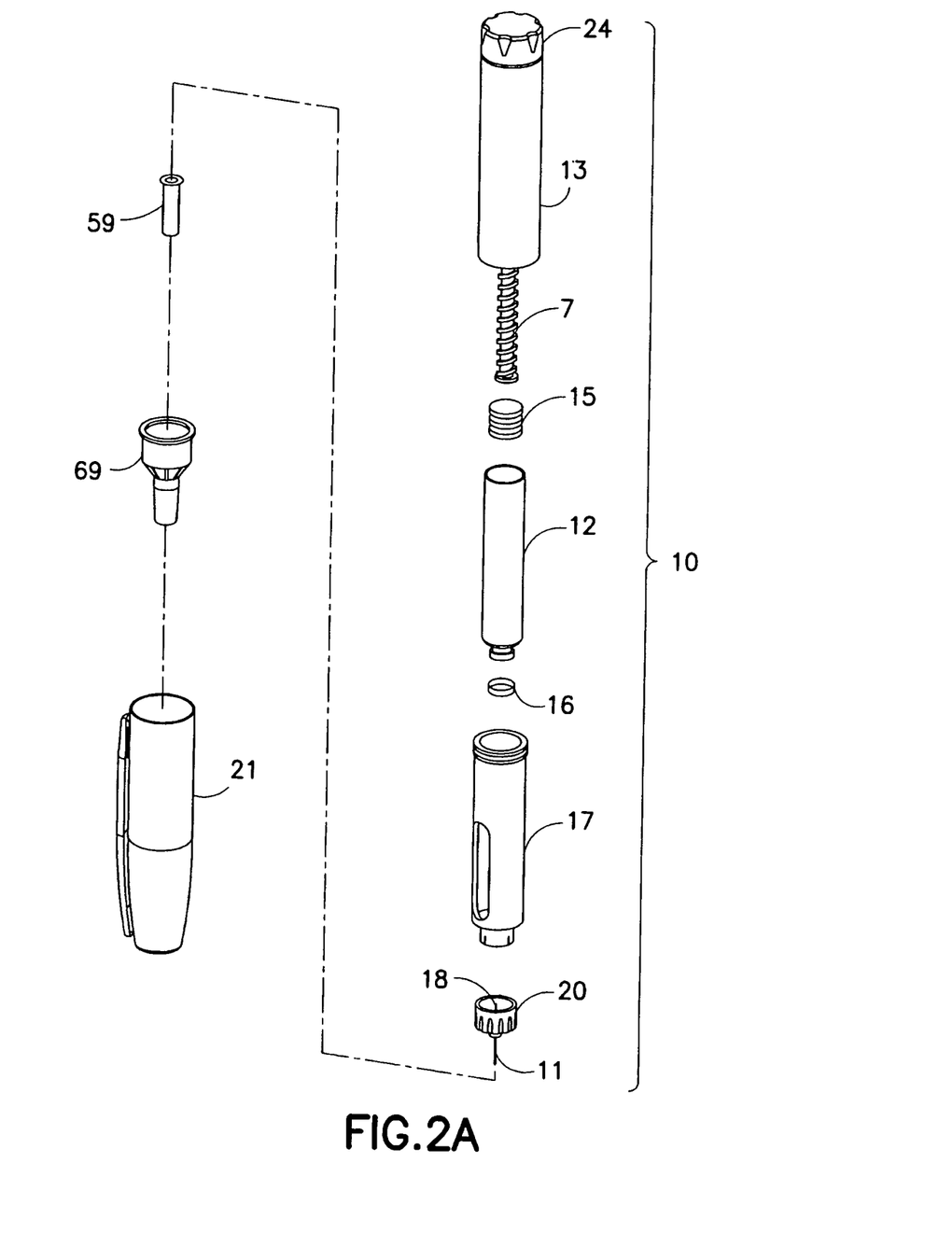
FIG. 2A is an exploded perspective view of the components of the drug delivery pen of FIG. 1.

FIG. 2A is an exploded view of the exemplary drug delivery pen 10 shown in FIG. 1, and typical components contained therein. At a distal end, the dose knob/button 24 is provided and has a dual purpose. The dose knob/button 24 is used to both set the dosage of the medication to be injected and to inject the dosed medicament via the lead screw 7 and stopper 15 through the medicament cartridge 12, which is attached to the drug delivery pen through a lower housing 17. In standard drug delivery pens, the dosing and delivery mechanisms are all found within the outer sleeve 13 and are not described in greater detail herein as they are understood by those knowledgeable of the prior art. The distal movement of the plunger or stopper 15 within the medicament cartridge 12 causes medication to be forced into the needle 11 of the hub 20. The medicament cartridge 12 is sealed by septum 16, which is punctured by a septum penetrating needle cannula 18 located within the hub 20. The hub 20 is preferably screwed onto the lower housing 17, although other attachment means can be used.

Figure 2B:
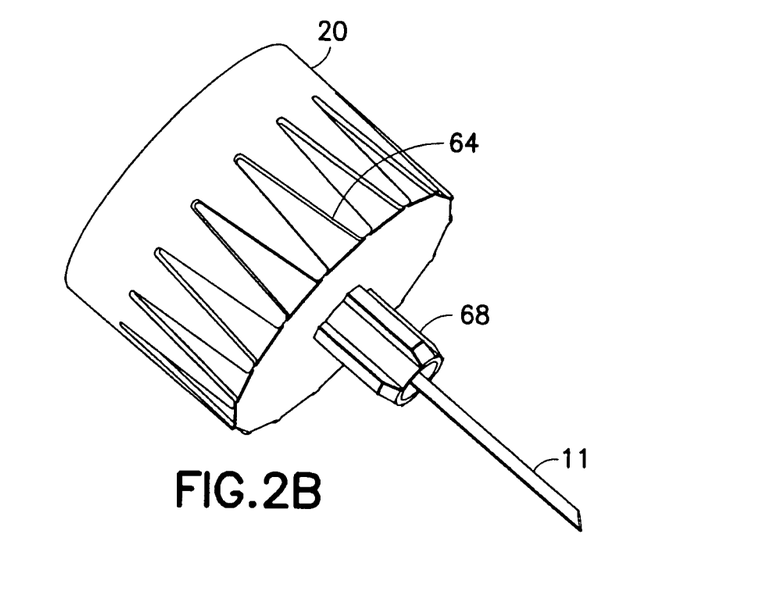
FIGS. 2B and 2C are perspective views of the pen needle for use with the drug delivery pen of FIG. 1.
Figure 2C:
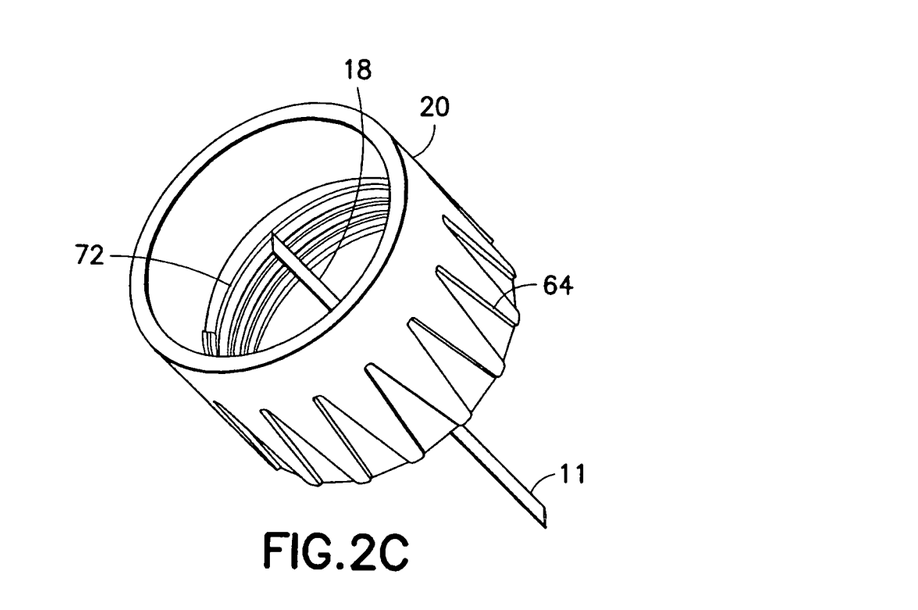

FIGS. 2B and 2C are perspective views of the pen needle of FIG. 2A in greater detail. As shown in FIG. 2B, the pen needle includes the hub 20 disposed at a non-patient end thereof which includes a plurality of ribs 64 for engagement with anti-rotation/retaining structures that will be described in greater detail below. In addition, protrusion 68 extends from a patient end of the hub 20 and the patient needle 11 extends from the protrusion 68. The septum-penetrating needle cannula 18 disposed within the non-patient end of the hub 20 fluidly communicates with the patient needle 11. Further, as shown in FIG. 2C, the interior of the non-patient end of the hub 20 includes threads 72 for connection with the pen injector. FIGS. 2A-2C illustrate one example of a pen needle.

To protect a user, or anyone who handles the drug delivery pen 10, an outer cover 69, which attaches to the hub 20, covers the hub when not in use. An inner shield 59 covers the patient needle 11 within the outer cover 69. The inner shield 59 can be secured to the hub 20 to cover the patient needle 11 by any suitable means, such as an interference fit or a snap fit. The cap 21 fits snugly against outer sleeve 13 to allow a user to securely carry the drug delivery pen 10. At a time of use, the cap 21, outer cover 69 and inner shield 59 are removed to expose the hub 20.

The medicament cartridge 12 is typically a tube sealed at one end with the septum 16 and sealed at the other end with the stopper 15. The septum 16 is pierceable by the septum penetrating cannula 18 in the hub 20, but does not move with respect to the medicament cartridge 12. The stopper 15 is axially displaceable within the medicament cartridge 12 to deliver the desired medicament amount while maintaining a fluid tight seal.

A pen needle, which includes the hub 20, needle 11, outer cover 69 and inner shield 59, is typically used for a single injection and is then disposed of. Typically, new pen needles are packaged individually and disposed loose in a container, such as a box or carton. Each pen needle is sealed in a package formed by the outer cover with a label covering the opening in the outer cover to identify the pen needle and provide a sterility barrier. However, containers of such packaged new pen needles do not include means for easily dispensing the new pen needles or containing used pen needles. Accordingly, a need exists for a storage assembly that easily dispenses new pen needles and stores both new and used pen needles.

Additionally, existing pen needle containers are configured to store a large number of packaged new pen needles. The large number of packaged new pen needles causes these containers to be large and bulky, such that the containers are not conducive to being carried by the user. Accordingly, a need exists for a storage assembly that is conveniently carried by a user.

SUMMARY OF THE INVENTION

In accordance with aspects of exemplary embodiments of the present invention, the above and other problems are substantially solved by providing a multi-pack assembly for containing and dispensing one or more new pen needles, and receiving and then safely and securely storing used pen needles after use.

In accordance with an aspect of the present invention, a housing is provided in which a plurality of both new and used pen needles can be contained in a series of storage vessels. An exemplary embodiment of such a housing can be, but is not limited to, a row-like configuration in which each storage vessel is secured to adjacent storage vessels forming a row of aligned, storage vessel.

In accordance with another aspect of the present invention, the housing can provide caps for each individual pen needle storage vessel that can be opened independently of one another, and can be closed after use to prevent unwanted interaction with the pen needle contained therein.

In accordance with another aspect of the present invention, the housing can provide pen needle storage vessels that are held together in a row-like configuration by a solid segment, which gives a basic structure and shape to the overall needle assembly.

In accordance with another aspect of the present invention, the housing can be constructed of a frangible material and the row-like configuration of storage vessels can be scored, indented or perforated between vessels to allow a user to separate the storage vessels into smaller segments as desired.

In accordance with another aspect of the present invention, the housing can provide caps for each pen needle storage vessel having a barrel hinge, a living hinge, or combinations thereof.

In accordance with another aspect of the present invention, a multi-pack assembly for containing and then dispensing one or more new pen needles, and receiving and then safely and securely storing used pen needles, can be provided by a device including a plurality of pen needles individually contained in a plurality of pen needle storage vessels connected by a solid segment in a row-like configuration. A sterility barrier can be formed by individual caps that fit over each individual pen needle storage vessel, covering the non-patient end of the new pen needle. Each individual pen needle storage vessel can be opened independently of one another, and can be closed after use to prevent unwanted interaction with the pen needle contained therein. The pen needle storage vessels can be held together by the solid segment, which gives the basic structure and shape to the overall needle assembly.

Objects, advantages, and salient features of the invention will become apparent from the following detailed description, which, taken in conjunction with the annexed drawings, discloses exemplary embodiments of the invention.

BRIEF DESCRIPTION OF THE DRAWINGS

The above benefits and other advantages of the various embodiments of the present invention will be more apparent from the following detailed description of exemplary embodiments of the present invention and from the accompanying figures, in which.

Throughout the drawings, like reference numbers will be understood to refer to like parts, components and structures.

DETAILED DESCRIPTION OF THE EXEMPLARY EMBODIMENTS

As noted above, new pen needles are typically packaged individually and disposed loose in a container, such as a box or carton. Each pen needle is sealed in a package formed by the outer cover with a label covering the opening in the outer cover to identify the pen needle and provide a sterility barrier. However, containers of such packaged new pen needles do not include means for easily dispensing the new pen needles or containing used pen needles. Additionally, existing pen needle containers are configured to store a large number of packaged new pen needles. The large number of packaged new pen needles causes these containers to be large and bulky, such that the containers are not conducive to being carried by the user.

Current pen needles are sold individually packaged inside a plastic cover, with a label adhered to the cover to identify the needle and provide a sterility barrier. However, a more convenient system and method is desired including a multiple needle package configuration that stores and provides new pen needles for use, and includes some provision for receiving and containing used pen needles after use. The exemplary embodiments of the present invention address these and other needs by providing a multi-pack assembly including multiple new pen needles in user accessible openings of the assembly, wherein covers or other enclosures are provided or positioned to enclose each new pen needle inside the user accessible openings of the assembly.

Figure 3:
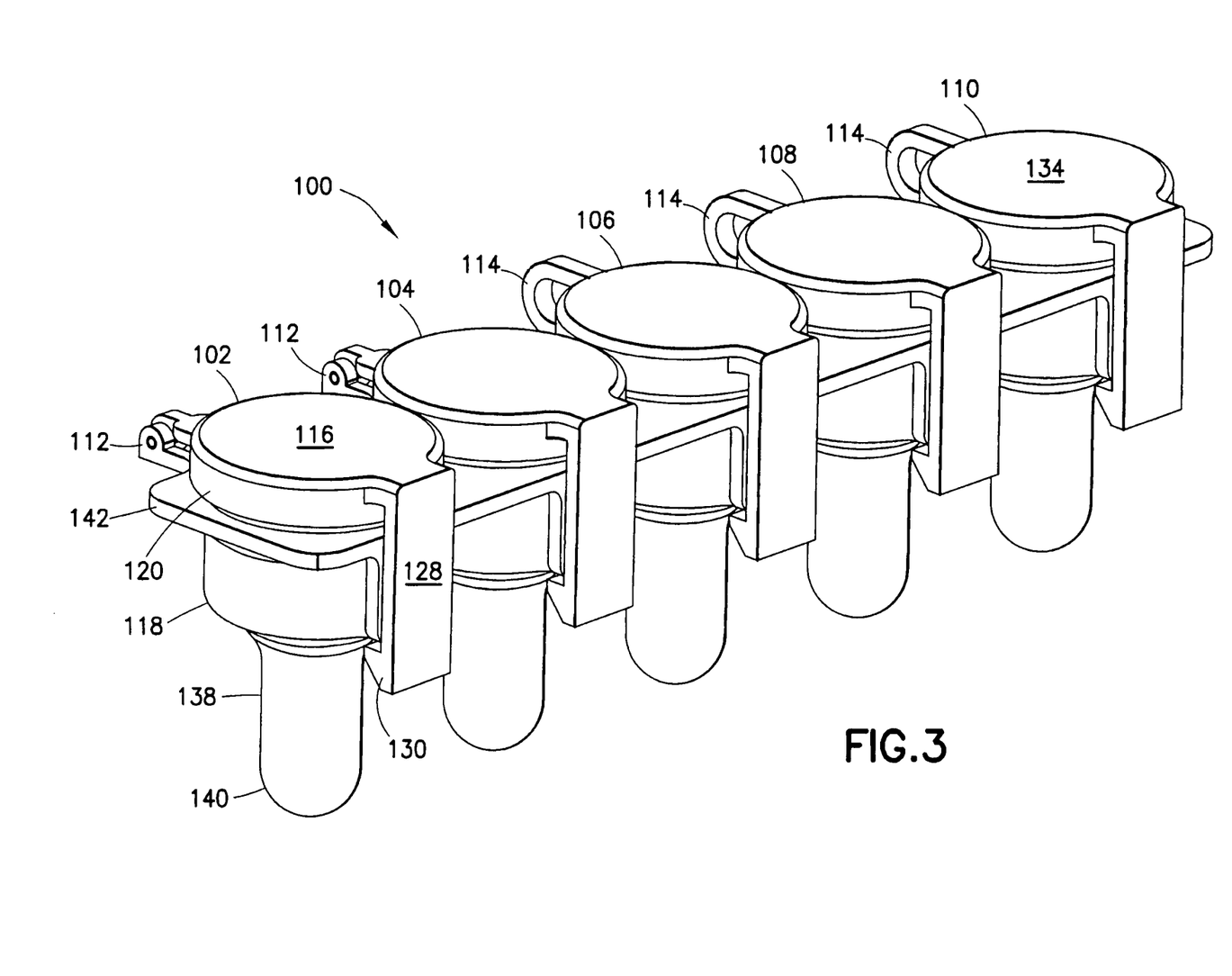
FIG. 3 is an enlarged perspective view of a pen needle containment device according to an exemplary embodiment of the present invention.
Figure 4:
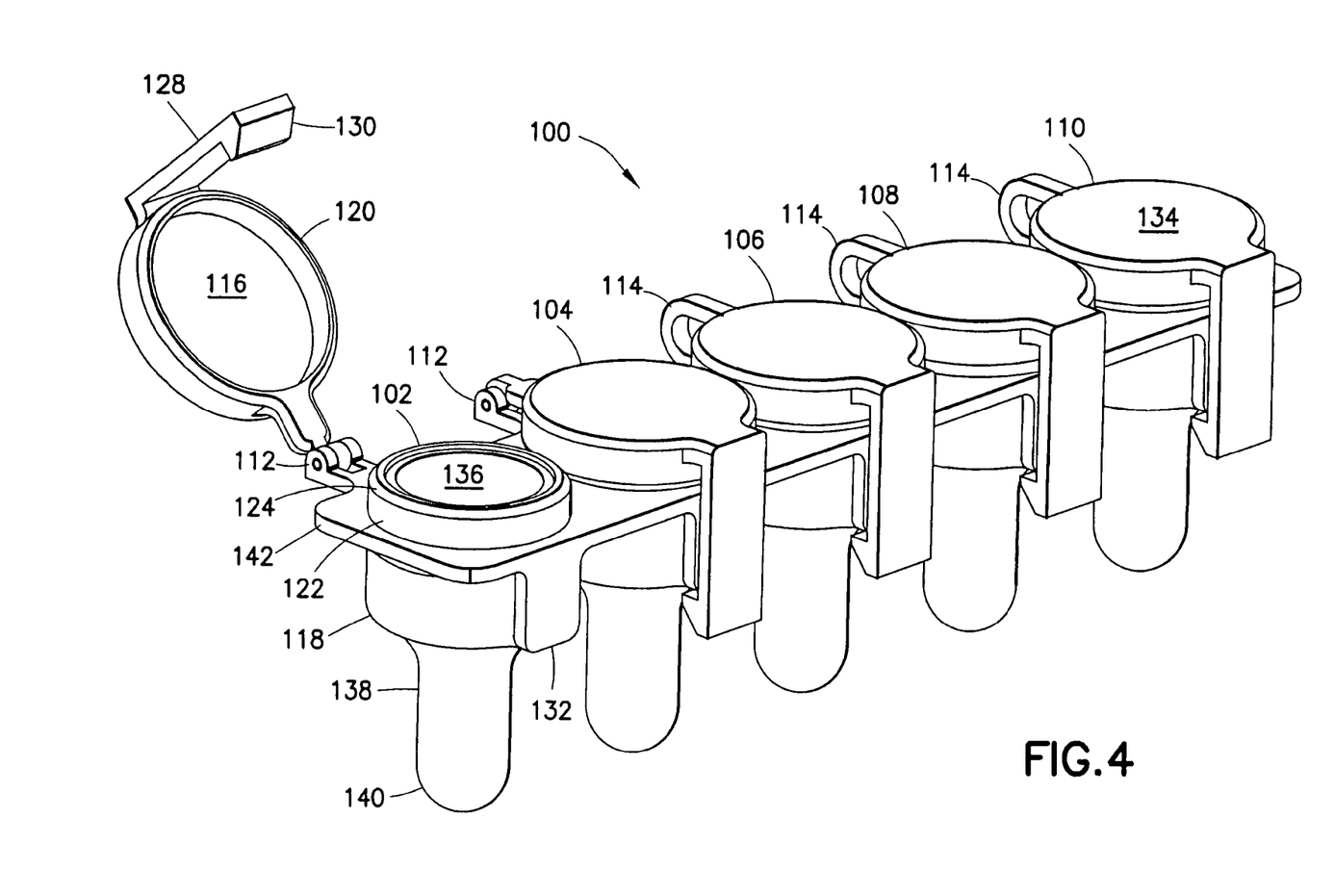
FIG. 4 is an enlarged perspective view of the device of FIG. 3 illustrating a single opened cap according to an exemplary embodiment of the present invention.
Figure 5:
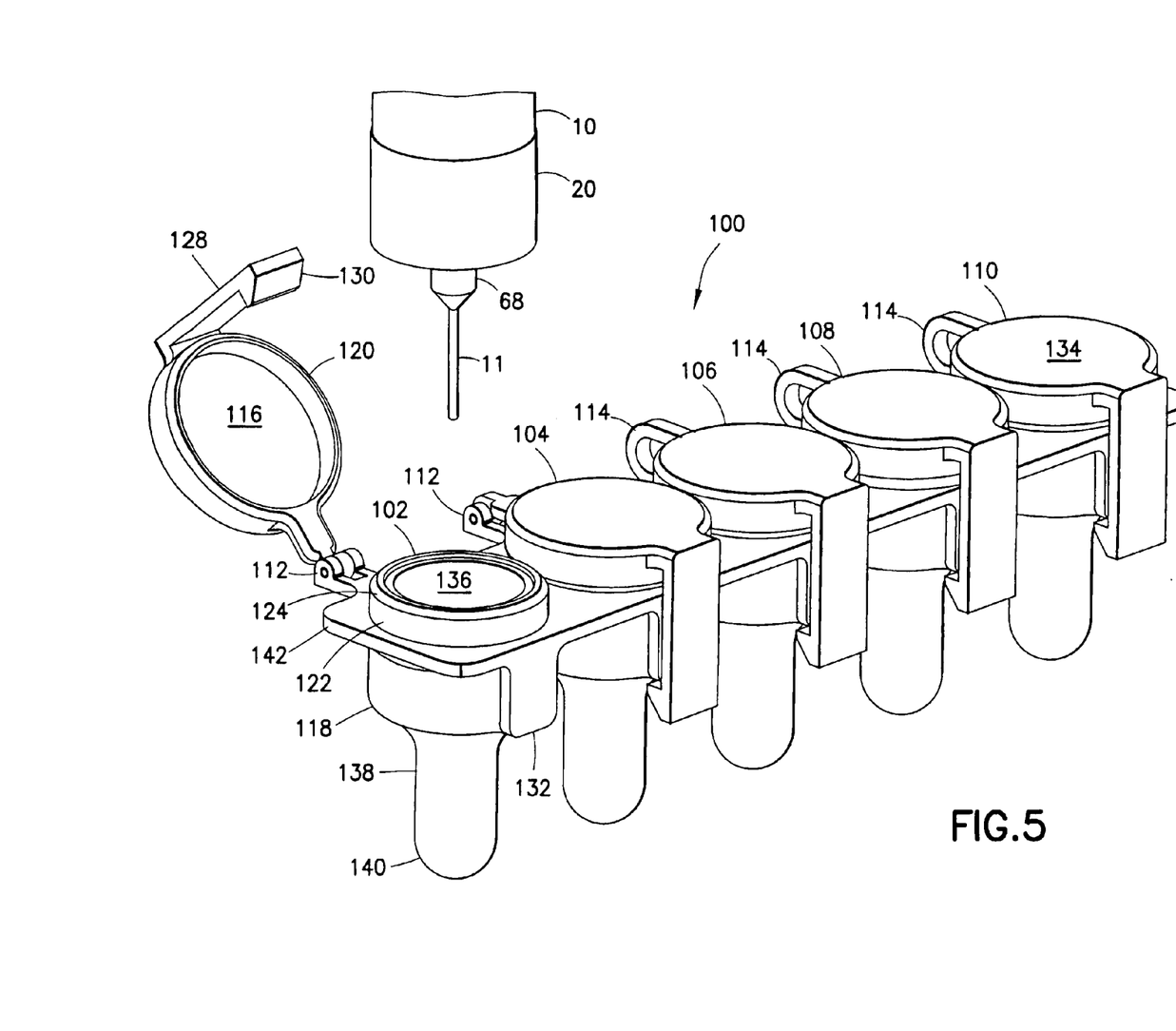
FIG. 5 is an enlarged perspective view of the device of FIG. 3 illustrating a single opened cap and removed pen needle according to an exemplary embodiment of the present invention.
Figure 6:
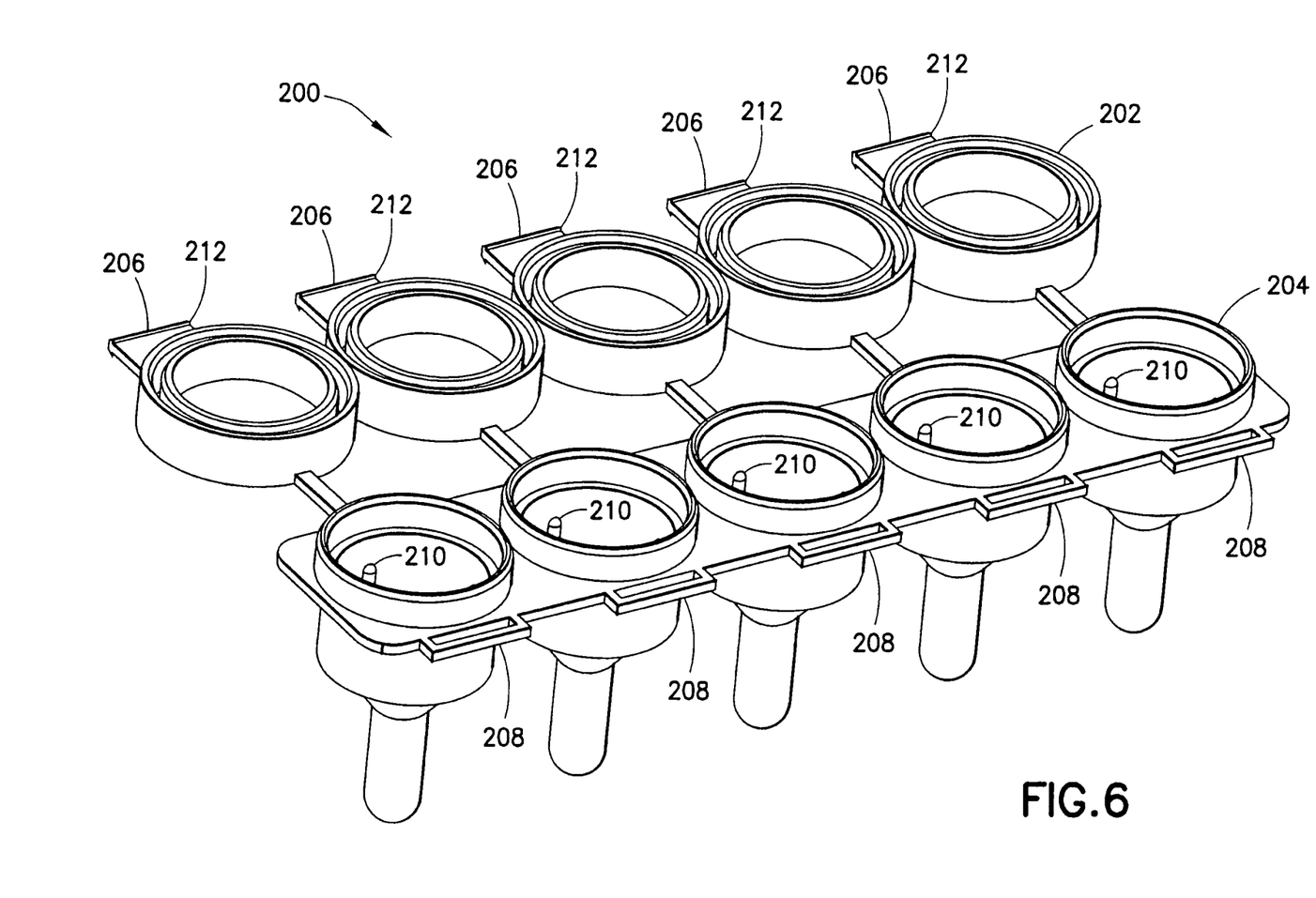
FIG. 6 is an enlarged perspective view of another embodiment of a pen needle containment device with all caps opened according to an exemplary embodiment of the present invention.

In a first exemplary embodiment of the present invention as shown in FIGS. 3-5, and a second exemplary embodiment of the present invention as shown in FIG. 6, a multi-pack assembly for containing and dispensing new pen needles, and receiving and containing used pen needles is provided. The exemplary embodiments of the present invention consist of a plurality of pen needle storage vessels connected by a solid segment in a row-like configuration. A sterility barrier is formed by individual caps that fit over each individual pen needle storage vessel, covering the non-patient end of the new pen needle. In an exemplary embodiment of the present invention, the caps for each individual pen needle storage vessel can be opened independently of one another using for example, a living hinge, and can be closed after use to prevent unwanted interaction with the pen needle contained therein. The pen needle storage vessels are preferably held together by the solid segment, which gives the basic structure and shape to the overall assembly. In yet other embodiments of the present invention, the solid segment can be perforated, weakened or frangible in some manner between storage vessels to allow the user to tailor the number of connected storage vessels that are to be carried by breaking the solid segment at some point.

An exemplary housing 100 of a multi-pack assembly for containing and dispensing new pen needles, and receiving and containing used pen needles is shown in FIG. 3. In a first exemplary embodiment of the present invention, the housing 100 comprises a plurality of pen needle storage vessels 102-110 that can be connected by a solid, segment 142 in a row-like configuration. In the exemplary embodiment shown in FIG. 3, five pen needle storage vessels 102-110 are shown, and are connected in a row-like configuration. However, in yet other embodiments of the present invention, any number of storage vessels can be provided, and arranged in any number of configurations.

In the exemplary embodiment, storage vessels 102 and 104 and hinges thereof are substantially the same and therefore, only storage vessel 102 will be described in further detail. Storage vessels 106-110 and hinges thereof are substantially the same and therefore, only storage vessel 110 will be described in detail. The storage vessels 102 and 110 illustrate a first and second exemplary embodiment of a hinge member 112 and 114, respectively, but are otherwise substantially the same. In yet other embodiments of the present invention, each of the storage vessels of the entire multi-pack assembly can comprise hinges 112, hinges 114, or any combination thereof.

In a first exemplary storage vessel 102, a cap 116 is provided which is rotatable about the hinge 112 for opening and closing a storage vessel body 118. The cap 116 is provided with a raised, substantially circular outer circumference 120 having a diameter and height sufficient to receive a similar raised, substantially circular outer circumference 122 of the vessel body 118. Each of the raised, substantially circular outer circumferences 120 and 122 are further provided with a chamfer 124 to aid in the rotatable engagement between the cap 116 and the vessel body 118.

The cap 116 is also provided with a flexible securing member 128 opposite the hinge 112, and extending substantially perpendicular to the cap 116. The flexible securing member 128 is preferably molded or formed with the cap 116, and comprises an inclined detent 130 extending from an end of the flexible member 128. The inclined detent 130 comprises an inclined surface and a shoulder to secure the cap 116 to the vessel body 118. Specifically, the flexible member 128 and inclined detent 130 are configured to engage a flat portion 132 of the vessel body 118 and be deflected away from the flat portion 132 when the cap 116 is being closed. At a completely closed position, the flexible member 128 and inclined detent 130 are elastically urged to return to a non-deflected position such that that the shoulder of the inclined detent 130 captures and releasably secures a shoulder of the flat portion 132. Further, the inclined detent 130 of the flexible member 128 is configured to extend slightly past the flat portion 132, thereby providing user access to the extended portion to aid in user deflection of the inclined detent 130 from the secured position to thereby open the cap 116.

Each cap is rotatably secured to the vessel bodies via flexible member, hinge, or other similar element. In a first exemplary embodiment, the cap 116 is rotatably secured to the vessel body 118 via an exemplary barrel hinge 112 and can be easily rotated between open and closed positions. Such a hinge 112 can be used in exemplary embodiments wherein the cap 116 is preferred to remain open or in position upon release. The exemplary cap 134 of storage vessel 110 is secured to the vessel body via an exemplary living hinge 114. The living hinge 114 can comprise a thin flexible piece to join the more rigid cap 134 to the storage vessel 110. Such a hinge 114 can be used in exemplary embodiments wherein the cap 134 is preferred to return to a position upon release. In yet other embodiments of the present invention, each of the storage vessels of the entire multi-pack assembly can comprise hinges 112, hinges 114, or any combination thereof.

As known to those skilled in the art, a living hinge is typically a thin flexible member that joins two rigid parts together, allowing them to bend along the line of the hinge with minimal friction and wear. Such hinges can be manufactured in an injection molding operation that creates all three parts at one time as a single unit, which can remain functional over the life of the hinge. Polyethylene and polypropylene are typically used for living hinges, due to their fatigue resistance.

Each storage vessel comprises an opening configured to store both new and used pen needles and is provided with an inner diameter sufficient to releasably secure the new and used pen needle and prevent rotation of the pen needle therein to aid in attachment and removal of the pen needle and the pen device. To do so, the vessel body of each, such as vessel body 118, comprises an opening 136 configured to releasably secure a hub 20 of a pen needle. The vessel body further comprises a reduced diameter portion 138 to releasably secure one or more of a hub portion and a pen needle 11. Finally, the vessel body further comprises a closed end 140 thereof with rounded features to aid in storage by a user.

Each vessel body of storage vessels is arranged and secured via a substantially flat, securing band 142 which is provided to secure each of the pen needle storage vessels 102-110 in a row-like configuration. Although a row-like configuration is shown, in yet other exemplary embodiments of the present invention, the pen needle storage vessels can be arranged and secured in a staggered row-like configuration, a double or multiple stacked row-like configuration, and/or in a manner wherein each pen needle storage vessel faces the same direction or faces opposite directions. In an exemplary embodiment, the securing band 142 comprises a substantially flat member molded or constructed of the same material as the storage vessels, and which gives the basic structure and shape to the overall needle storage assembly. In yet other embodiments of the present invention, the solid segment 142 can be perforated, weakened or frangible in some manner to allow the user to tailor the number of connected storage vessels that are to be carried by breaking the solid segment 142 at some point.

FIG. 5 is a perspective view of the device of FIG. 3 illustrating a single opened cap and removed pen needle according to an exemplary embodiment of the present invention. As shown in FIG. 5, the new pen needle has been removed from the housing 100 for use, by engagement with a drug delivery pen 10 of FIG. 2A. The drug delivery pen 10 can be threaded to, or otherwise secured to the new pen needle for removal from the housing. An inner shield may not be required in each case, as the reduced diameter portion 138 can be configured to releasably secure the protrusion 68 from which the patient needle 11 extends. Upon completion, the user can then simply return the used pen needle to the housing 100 and more specifically, to the empty vessel 118 for storage. As noted above, the vessel 118 can also provide features to prevent rotation of the pen needle when positioned in the vessel such that the user can simply unscrew or otherwise release the pen needle from the drug delivery pen and close the cap 116 for storage.

In an exemplary embodiment of the present invention, the caps for each individual pen needle storage vessel can be opened independently of one another, and can be closed after use to prevent unwanted interaction with the pen needle contained therein. The pen needle storage vessels are held together by the solid segment, which gives the basic structure and shape to the overall needle assembly. FIG. 6 is a perspective view of another embodiment of a pen needle containment housing 200 with all caps opened according to an exemplary embodiment of the present invention.

In the exemplary embodiment shown in FIG. 6, another exemplary cap assembly embodiment 202 is shown wherein each cap is secured to each respective storage vessel, and can be opened and closed individually to cover the storage vessels 204 substantially as described above in regard to FIGS. 3-5. Such an arrangement can further allow the use of alternate closing elements, such as the tabs 206 and slotted members 208. In the exemplary embodiment shown, multiple tabs 206 and slotted members 208 are shown, which can be engaged during closure of the caps. In the exemplary embodiment shown, the tabs 206 can be deflected into each opening 208, respectively, to capture the tabs in the openings. The tabs can be easily deflected by the user to permit release of the tabs from the openings to open the caps. A detent or expanded portion 212 can be provided at an end of each tab 206 to secure the tabs within the openings when inserted therein. The remaining features of the pen needle containment housing 200 are substantially the same as described above in regard to the pen needle containment housing 100.

In each of the storage vessels 204, a protrusion or other feature 210 is provided as anti-rotation and/or general friction projections to secure the pen needles and/or hubs thereof in each opening. In doing so, the protrusion 210 releasably secures the pen needle or hub in the opening to prevent the pen needle from simply falling from an open vessel, and to secure the pen needle to allow the threaded engagement or disengagement with the drug delivery pen 10, such as when a new pen needle is being withdrawn and when a used pen needle is being returned for storage. The protrusion 210 can comprise a detent disposed upon an inner wall of the opening of the storage vessel to work in conjunction with the hub of a pen needle to prevent rotation of the pen needle when the pen needle is in a dispensing position. For example, when the pen needle is in the dispensing position within the storage vessel and the anti-rotation/retaining features 210 are engaged with the ribs 64 (see FIGS. 2B and 2C) of hub 20, the anti-rotation/retaining features 210 prevent the pen needle from rotating and permit the user to connect a pen injector or a medicament cartridge to the hub by threading the pen injector or medicament cartridge into the threads 72 of the hub 20. While preventing rotation of the pen needle during connection to the pen injector, subsequent to the connection, the fit between the anti-rotation/retaining features 210 and the pen needle permits the user to axially withdraw the combined pen injector and pen needle from the storage vessel.

Conversely, when returning the used pen needle to the storage vessel, the user axially inserts the pen needle into the storage vessel to engage the ribs 64 of the hub 20 with the anti-rotation/retaining features 210. Subsequent to the engagement, the user rotates the pen injector to unthread the pen injector from the threads 72 of the hub 20, thereby disengaging the pen injector from the pen needle. The fit between the anti-rotation/retaining features 210 and the pen needle provides some resistance to removal of the pen needle from the storage vessel and prevents the pen needle from simply falling out of the storage vessel.

Further, in yet other exemplary embodiments of the present invention, a single cover (not shown) can be provided that can snap on and off of the entire assembly to cover the cavities therein. In still other exemplary embodiments of the present invention, each individual cover or single cover can be provided in a tongue-and-groove or dovetailed manner such that the cover(s) can slide on and off to cover the cavities therein. A detent or other friction can be provided to hold the sliding covers in one or more positions.

In each of the exemplary embodiments described above, a sterility barrier is formed by the individual caps that fit over each storage vessel, covering the non-patient end of the new pen needle contained therein. The caps can be sealed to the storage vessel in some manner prior to a first opening, or the presence of the closed cap can provide sterility of each new pen needle via tortuous path. However, covers and/or seals can be used in combination with the caps to enhance protection. For example, a cover (not shown), such as a paper, foil, or plastic label can also be used as the primary or sole sterility barrier for each individual new pen needle. In such an embodiment, in order to cover the used pen needles, a separate piece can be used to cover the non-patient ends of the returned needles, such as a slide that can be moved out of the way to access new pen needles.

Further, in these or other exemplary embodiments of the present invention, a system and method can be provided to distinguish new from used pen needles or the storage thereof. For example, in one embodiment, a paper tape can be provided on the top of the covers. Once a cover is opened, the opening breaks part of the tape, thereby indicating that the cap has been opened and showing that the needle therein has been removed or has been used.

Pen needles of the exemplary embodiments can be manufactured using existing processes and subsequently assembled into the housings of the exemplary embodiments of the present invention, thereby simplifying the manufacturing process. The overall size of the exemplary embodiments of the present invention is minimized by allowing used pen needles to be stored in substantially the same spaces previously used to store the new needles. Further, the exemplary embodiments of the present invention can be constructed having a size and shape, and contoured edges, to increase the comfort of the user during transportation, such as in a user's pocket.

As noted above, FIGS. 2B and 2C are perspective views of the pen needle of FIG. 2A wherein the pen needle includes the hub 20, protrusion 68 and patient needle 11. The septum-penetrating needle cannula 18 disposed within the non-patient end of the hub 20 fluidly communicates with the patient needle 11, and the interior of the non-patient end of the hub 20 includes threads or other features 72 for connection with the pen injector. In these or other exemplary embodiments of the present invention the pen needle can omit one or more of the above features as long as sterility of both the patient and non-patient ends of the cannula is maintained. For example, an exemplary pen needle can also be provided having a hub and cannula assembly only.

In the exemplary embodiments of the present invention, the multi-pack assembly housings 100 and 200, and hinges thereof including the living hinge, can be constructed of one or more of a polycarbonate, polyethylene, polypropylene and acrylonitrile butadiene styrene material, but are not limited thereto. Further, the multi-pack assembly housings 100 and 200 and/or caps thereof can be color-coded to simplify identification of the new pen needles stored therein.

Further, in these or other exemplary embodiments of the present invention, a lock-out system and method can be provided such that after the use of the final needle, the user can manually lock the multi-pack assembly housings 100 and 200 (i.e., manually lock the multi-pack assembly housings closed) to allow for safe disposal. For example, a manual lock can be provided on the needle storage assembly, thereby allowing the user to manually lock the storage assembly after final use to allow for safe disposal thereof. To do so, the latches described above can be configured to prevent re-opening by the user once fully closed. The latches of 128-132 and 206-208 can be configured to irreversibly lock once fully closed to prevent opening and re-use of a non-new pen needle.

However, in these and other exemplary embodiments of the present invention, an emergency needle feature can be provided wherein at least one new or used needle can remain accessible, such that the user has access to the at least one of the new or used needles for use in case of an emergency. Alternatively, in yet other embodiments of the present invention, only one needle can be provided as always accessible, thereby providing an available needle for use in case of emergency. The other pen needles can be locked into the storage assembly and can no longer be accessible.

The foregoing embodiments and advantages are merely exemplary and are not to be construed as limiting the scope of the present invention. Various modifications, alternatives and variations will be apparent to those of ordinary skill in the art, and are intended to fall within the scope of the invention as defined in the appended claims and their equivalents.

What is claimed is:

1. An assembly for storing both new and used pen needles of an injection apparatus, comprising:
   a planar segment;
   a plurality of storage vessels, wherein each of said storage vessels is secured to said planar segment and comprises an enlarged open proximal end and a closed distal end, wherein said planar segment comprises a width and a length not less than an outside diameter of said enlarged open proximal end;
   a cap for each individual storage vessel, wherein each cap comprises an opening to releasably receive therein said enlarged open proximal end of said storage vessel; and
   a hinge for rotatably coupling each of said caps to said planar segment.

2. The assembly for storing both new and used pen needles of an injection apparatus as recited in claim 1, wherein said planar segment is configured to secure each of said storage vessels to an adjacent storage vessel.

3. The assembly for storing both new and used pen needles of an injection apparatus as recited in claim 1, further comprising a flexible securing member extending substantially perpendicular to each cap, said flexible securing member comprising an inclined detect extending from an end of said flexible securing member to releasably secure said cap to said storage vessel.

4. The assembly for storing both new nevi and used pen needles of an injection apparatus as recited in claim 2, further comprising:
   a flexible securing member extending from said cap, and
   wherein said segment comprises a receiving opening for each of said securing members, respectively, to releasably secure said caps to said storage vessels.

5. The assembly for storing both new and used pen needles of an injection apparatus as recited in claim 2, further comprising:
   a flexible securing member extending from said cap, and
   wherein said segment comprises a receiving opening for each of said securing members, respectively, to irreversibly secure said caps to said storage vessels.

6. The assembly for storing both new and used pen needles of an injection apparatus as recited in claim 1, wherein said planar segment is frangible between said storage vessels to allow separation.

7. The assembly for storing both new and used pen needles of an injection apparatus as recited in claim 1, wherein said hinges comprise barrel hinges, living binges, or a combination of barrel and living hinges.

8. The assembly for storing both new and used pen needles of an injection apparatus as recited in claim 7, wherein said planar segment, said storage vessels, said caps and said hinges are molded as a single piece.

9. The assembly for storing both new and used pen needles of an injection apparatus as recited in claim 1, wherein said enlarged open proximal end of each storage vessel comprises one or more detents for holding a pen needle in said storage vessel and preventing rotation of said pen needle.

10. The assembly for storing both new and used pen needles of an injection apparatus as recited in claim 1, wherein said closed distal end of said storage vessel is configured to releasable secure a distal end of said pen needle.

11. The assembly for storing both new and used pen needles of an injection apparatus as recited in claim 1, wherein said caps form sterility barriers for each individual pen needle storage vessel.

12. The assembly for storing both new and used pen needles of an injection apparatus as recited in claim 1, wherein said assembly is constructed of one or more of a polycarbonate, polyethylene, polypropylene and acrylonitrile butadiene styrene material.

13. The assembly for storing both new and used pen needles of an injection apparatus as recited in claim 1, wherein:
   said storage vessels are arranged in a row-like configuration.

* * * * *